United States Patent [19]
Chu et al.

[11] Patent Number: 5,440,927
[45] Date of Patent: * Aug. 15, 1995

[54] FIBER OPTIC MOISTURE SENSOR

[75] Inventors: Ling Chu, Chelmsford, Mass.; Henrik Pedersen, North Brunswich, N.J.

[73] Assignee: Rutgers, The State University of New Jersey, New Brunswick, N.J.

[ * ] Notice: The portion of the term of this patent subsequent to Jun. 14, 2011 has been disclaimed.

[21] Appl. No.: 201,820

[22] Filed: Feb. 25, 1994

Related U.S. Application Data

[62] Division of Ser. No. 914,795, Jul. 16, 1992, Pat. No. 5,319,975.

[51] Int. Cl.$^6$ .............................................. G01N 3/00
[52] U.S. Cl. .................................. 73/335.01; 250/365; 250/458.1
[58] Field of Search ............... 73/335.01, 29.05, 29.01; 250/361 R, 362, 363.01, 365, 458.1, 461.1, 573, 372; 422/88, 91

[56] References Cited

U.S. PATENT DOCUMENTS

| | | | |
|---|---|---|---|
| 4,173,432 | 12/1992 | Lefkowitz et al. | 422/91 |
| 4,749,856 | 6/1988 | Walker et al. | 73/335.01 |
| 4,988,212 | 1/1991 | Sun et al. | 374/161 |
| 5,043,285 | 8/1991 | Surgi | 422/91 |
| 5,319,975 | 6/1994 | Pederson et al. | 73/335.01 |

*Primary Examiner*—Robert Raevis
*Assistant Examiner*—Michael J. Brock
*Attorney, Agent, or Firm*—Louis M. Heidelberger; Reed Smith Shaw & McClay

[57] ABSTRACT

This invention provides for a fiber optic moisture sensor. The sensor is comprised of a housing and a support positioned within the housing. The support is coated with a film. A first and second light guides are positioned within the housing and communicate illumination to and from the film. A reflective surface is positioned within the housing facing the film. The film comprises an optically transparent polymer and a salt complex of a metal ion and an organic compound. The salt complex is capable of absorbing moisture and emits a fluorescence signal when excited by light at the appropriate wavelength. The fluorescence signal can be quenched when the salt complex absorbs moisture. An apparatus incorporating the sensor and a method of making the sensor are also provided.

1 Claim, 5 Drawing Sheets

FIBER OPTIC MOISTURE SENSOR

CROSS-REFERENCE TO RELATED APPLICATION

This a divisional of application Ser. No. 07/914,795, entitled "FIBER OPTIC MOISTURE SENSOR" filed Jul. 16, 1992, now U.S. Pat. No. 5,319,975.

BACKGROUND OF THE INVENTION

Humidity measurements are important in many industrial operations including food processing, the manufacture of plastic, paper and fine chemicals and in the production of semiconductors. In several biochemical processes where water activity or moisture levels are vital to the metabolic productivity of microorganisms, moisture levels must be determined in a fast, accurate, reliable manner, and on a real-time basis. Over the past few years, different types of humidity sensors have been developed and the recent trend has been to place such sensors in an in-line system for the detection and control of moisture levels.

Generally, moisture sensors incorporate a sensing material with an appropriate transducer. Sensing of moisture is achieved by interaction of the water molecules with the sensing material and the resulting electrical or optical signal is relayed to a detection system via a transducer. For example, Hijikigawa et. al in "A Thin-Film Resistance Humidity Sensor", Sensors and Actuators, 1983, 4, pages 307-315 have developed a humidity sensor consisting of a thin film coating on alumina substrate. The film is a composite made from crosslinked polystyrene-sulfonate covered with a protective film of cellulose ester. The film electrical resistance is sensitive to humidity.

In another example, Y. Sakai et al. "Humidity-Sensitive and Water-Resistive Polymeric Materials", Sensors and Actuators, 1988, 16, pages 359-367 discuss a two-polymer system comprising polytetrafluoroethylene vinylpyridine graft copolymer (PTFE-VP) and cross-linked polyvinylpyridine with 1,4-dibromobutane. The impedance of the two-polymers changes with the relative humidity.

As an example of ceramic or metal oxide based sensors, Y. Sadoka et. al "Electrical Properties of Anodized Aluminium in a Humid Atmosphere", Journal of Materials Science, 1986, 21, pages 1269-1274 have investigated anodized aluminium for the measurement of humidity. On the other hand, S. Mukode et al. in "A Semiconductive Humidity Sensor", Sensors and Actuators, 1989, 16, pages 1-11, discuss the use of semiconducting materials such as stannic and titanic oxides.

Cobalt chloride ($CoCl_2$) has been extensively used as a specific optical indicator for humidity. Anhydrous cobalt chloride is blue and changes to pink when hydrated. Generally, cobalt chloride based sensors have limitations and different concentrations of cobalt chloride are needed to measure a wide range of humidity levels. Other limitations include poor stability and reproducibility, variable accuracy, a limited temperature range, and a slow response time. Cobalt chloride based sensors may not be appropriate in many industrial situations.

Russell et. al in "Optical Sensor for the Determination of Moisture", Analytica Chimica Acta, 1985, 170, pages 209-216, report embedding cobalt chloride into a gelatin matrix and coating the matrix onto a 600 $\mu$m optical fiber to produce a humidity sensing system. The change in relative humidity is related to the absorption of light by $CoCl_2$ at 680 nm. The light is transmitted to the fiber and is then reflected internally.

Ballantine et. al in "Optical Waveguide Humidity Detector", Analytical Chemistry, 1986, 58(13), pages 2883-2885, also use cobalt chloride, in conjunction with a glass capillary tube. The cobalt chloride is incorporated into polyvinylpyrrolidone (PVP). The sensor is coupled to light emitting diodes and calibrated by monitoring the change in light absorption by cobalt chloride at a given wavelength.

Zhou et. al in "Porous Fiber-Optic Sensor for High-Sensitivity Humidity Measurements", Analytical Chemistry, 1988, 60(20) pages 2317-2320 discuss a humidity sensor using cobalt chloride incorporated into a porous glass fiber with a high surface area. The sensitivity of the sensor is dependent on the concentration of cobalt chloride. At low concentrations of cobalt chloride, the sensor is able to measure at low relative humidity. By increasing the concentration of cobalt chloride, the sensor is able to measure high relative humidity.

In other applications, Harris et. al in "Colorimetric Detection of Humidity and Other substances with Solvatochromic Dyes Dispersed in Porous Polymer Films", NASA Tech Briefs, MFS-26128, discuss thin polymer films containing solvatochromic dyes sensitive in their UV-Visible absorption spectrum to atmospheric water content. Detection of a color change can be achieved visually by comparison with a standard chart or spectrophotmetically by measurment of the wavelength of absorbance.

In other applications, sensors based on fluorescence have been used. Generally fluorescence-based moisture fiber optic sensors have demonstrated poor sensitivity especially at low relative humidity and respond slowly to changes in relative humidity. These limitations are due to the dynamic range of the reagents or dyes used. For example, Posch et. al in "Fiber-Optic Humidity Sensor Based on Fluorescence Quenching", Sensors and Actuators, 1988, 15, pages 77-83, report a fiber optic humidity sensor based on fluorescence quenching. Two different fluorescent dyes are used as humidity indicators: perylenedibutyrate and perylenetricarboxylic acid bis-imidates (PTCABs). A silica gel sheet is used to absorb the dyes and is subsequently cast onto a glass slide which is attached to a bifurcated fiber optic light guide to form a sensing system. Sensor sensitivity is poor at the high range of relative humidity and the response time is slow. Furthermore, gases such as oxygen and ammonia interfere with the desired, water mediated quenching mechanism.

Zhu et al. in "A New Fluorescence Sensor for Quantification of Atmospheric Humidity", Journal of Electro Chemical Society, 1989, 136, pages 657-570, report a fiber optic humidity sensor. The fluorescent dye rhodamine 6G (R6G) is impregnated in a Nafion polymer and is sensitive to changes in relative humidity. The sensor has limited sensitivity at relative humidities below 40%.

SUMMARY OF TEE INVENTION

It is an object of this invention to provide a fiber optic moisture sensor that can be applied to selectively detect moisture present in a wide range of phases.

It is another object of this invention to provide an apparatus incorporating the sensor of the invention.

It is yet another object of this invention to provide a method for making the sensor of the invention.

It is yet another object of this invention to provide a sensor with a fast response time.

It is yet a further object of the present invention to provide a sensor that is relatively stable.

These and other objects are accomplished by a fiber optic sensor comprising a housing and a support having a first face and a second face within said housing. The first face of the support is coated with a film. A first light guide and second light guides capable of communicating illumination to and from said film are incorporated within the housing. The sensor further comprises a reflective surface incorporated within the housing. The film comprises an optically transparent polymer and a salt complex of a metal ion and an organic compound. The salt complex is capable of absorbing moisture.

DETAILED DESCRIPTION OF THE PREFERRED EMBODIMENTS

Figure 1:
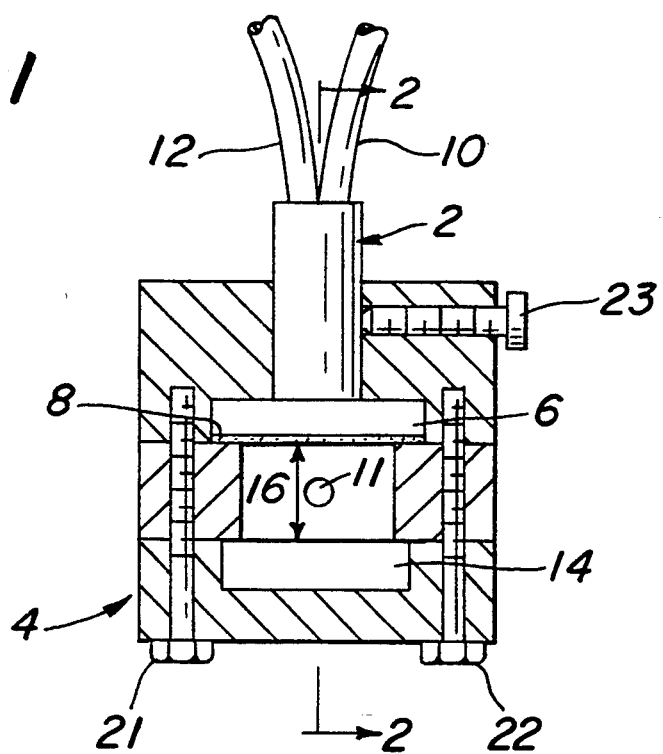
FIG. 1 is a diagram of a sensor of the present invention.

The sensor of the present invention operates on the principle that water molecules in the form of moisture or humidity quench the emitted signal produced by light excitation of a salt complex of a metal ion and an organic compound. More particulary, as it pertains to this invention, the emitted signal can be caused by fluorescence. Generally, fluorescence quenching refers to any process that results in the decrease of fluorescence intensity or in the decrease of the quantum yield of fluorophores upon interaction with other chemical species. More particularly, as it pertains to this invention, fluorescence quenching is the result of the interaction of specific fluorophores with water molecules. With the sensor of the present invention, detection of moisture as a change in relative humidity using fluorescence quenching can be achieved and relative humidity levels as a function of fluorescence intensity can be qualified according to mathematical relationships known in the art, such as for example, the Stern-Volmer relationship which linearly relates changes in inverse fluorescence intensity and relative humidity levels.

The sensor of the present invention can be comprised of a film comprising a salt complex of a metal ion and an organic compound and the film can be coated onto a support. The salt complex of a metal ion and organic compound can emit a fluorescence signal when it is excited by light at the appropriate wavelength. The fluorescence signal can be quenched when the salt complex absorbs water molecules. Changes in the fluorescence signal can be measured and monitored by means for fluorescence detection which are known in the art. The water molecules can desorb and the sensor can operate in a reversible manner.

Generally, a salt complex of a metal ion and organic compound can be selected for its ability to absorb humidity and additionally for its ability to excite and emit light at an appropriate wavelength. More specifically, salt complexes of a metal ion and organic compound which can form a hydration complex as well as contain a metal ion for which an optical assay can be performed can be used in the sensor of the present invention. The optical assay can rely on fluorescence or absorbance. Metal ion salts such as aluminium, calcium and iron sulfates or aluminium, calcium, iron and cobalt chlorides can be used to provide the metal ion. Generally, optical methods for detection of the metal ion can rely on organic O,O-donating, O,N-donating and N,N-donating chelating reagents such as for example pyrocatechol violet, morin, lumogallion, poly(macrocyclic) compounds, 1,2,4-trihydroxyanthraquinone, calcein and various porphyrins.

In one embodiment of the invention, an organic complex such as morin (3,5,7,2',4'-pentahydroxyflavone) can be used. Morin can form a highly fluorescent complex with a metal ion such as for example aluminium, beryllium, a salt complex of zinc, gallium, indium and scandium. More specifically, the aluminium and morin salt complex can be used and is highly fluorescent at about 505 nm when excited at about 420 nm. When the salt complex of aluminium and morin absorbs water, the fluorescence can be quenched and the change in relative humidity can be correlated to the intensity of the quenched signal.

In another embodiment of the invention, an organic complex such as lumogallion (4-chloro-6-(2,4-dihydroxy-naphtalazo)-1-hydroxybenzene-2-sulfonic acid monosodium salt) can be used. Lumogallion forms a highly fluorescent complex with a metal ion such as for example aluminium. More specifically a salt complex of aluminium and lumogallion can fluoresce at about 600 nm when exited at about 490 nm.

The salt complex of aluminium and morin can be formed by dissolving aluminium sulfate and morin with a suitable solvent and then mixing by using mechanical agitation. A solvent system can be used which comprises a solvent such as acetone or acetone and water in a volume ratio of from about 1:1 to about 3:1, preferably of from about 1:2 to about 3:2 can be used. Other solvents which can be used include methanol, ethanol and isopropanol alone or in combination with water.

Following dissolution and mixing, the salt complex can be embedded into a film, preferably comprising a polymer such as for example poly(vinylpyrrolidone) (PVP). The polymer can be selected such that it is optically transparent in the wavelength range. Other optically transparent polymers which can be used include cellulose, silicone rubber, poly(vinyl-chloride), and poly(vinylalcohol). Alternatively, polymers which are not optically transparent can also be used provided such polymers are permeable to water. In the case of non-optically transparent polymers such as for example porous Teflon and Nafion, the optical signal can be based on surface fluorescence.

The polymer can be added to the solution mixture of the salt complex such that the amount of the salt complex can vary of from about 5 to about 20% on a weight per volume basis of the solution mixture. The ratio of polymer to the salt complex can be dependent on the desired sensitivity of the sensor and the mechanical strength of the film. The resulting polymer solution which comprises the salt complex can form a film upon coating onto a support. Preferably, an optically transparent support such as for example silica can be used. The support can be of any shape including, for example, square or circular and its surface area can be only limited by the level of sensor miniaturization which is required.

Prior to coating, the support can be washed with a dilute solution of a mineral acid, (for example hydrofluoric acid) of from about 1 to about 2% on a volume basis and for about 2 minutes. After the acid wash, the support can be washed with water for about 5 minutes. The support can be dried and partially covered with the polymer solution using techniques known in the art such that a film can be deposited. The film can be of any shape and of any thickness. The only limitation on the shape is the level of miniaturization required, however, the shape of the film is preferably circular. In a preferred embodiment, the film thickness can be of from about 10 to about 40 $\mu$m, preferably less than about 20 $\mu$m for optimum sensor response.

In addition to the salt complex of aluminium and morin, other complexes of a metal ion and organic compound can be used. For example, a salt complex of berrylium and morin, aluminium and quercetin, salt complexes of a metal ion and 1-(2 Hydroxy-4-sulfo-1-naphtylazo)-2-naphtol-3,6-disulfonic acid (hydroxynaphthol blue) and salt complexes of a metal ion and 8-hydroxyquinoline-5-sulfonate can also be used. Other salt complexes that can be used include complexes of a metal ion such as calcium, nickel, copper and cobalt and complexes of a metal ion and an organic compound comprising the o,o'-dihydroxyazo functional group.

FIG. 1 shows a sensor of the present invention. The sensor is comprised of a probe 2 incorporated into a housing 4. Probe 2 is comprised of a support 6 covered with film 8 and first and second optical fibers 10 and 12. Support 6 is positioned flush with the first end of first optical fiber 10 which is capable of communicating excitation light to film 8 and is positioned flush with the first end of second optical fiber 12 which is capable of communicating emission light from film 8.

Optical fibers 10 and 12 can be used either singly or in multitude as a bifurcated optical fiber bundle. Generally, optical fibers 10 and 12 can be selected such that they transmit light within the appropriate wavelength range based on the salt complex used.

For example, when a salt complex of aluminium and morin is used a fiber optic bundle (manufactured by EOTec Corporation, New Haven, Conn.) with a core diameter of 48 $\mu$m, a clad diameter of 50 $\mu$m, a buffer diameter of 1.78 mm and a numerical aperture of 0.56 can be used.

To enhance light communication into first and second optical fibers 10 and 12 as shown in FIG. 1, optionally, a reflective surface such as for example mirror 14 can be used. Mirror 14 can be positioned facing and parallel with film 8. Generally, mirror 14 can be selected such that the distance 16 between film 8 and mirror 14 is about equal to the focal length of mirror 14. Mirror 14 can be of any size and focal length, however both the size and focal length of mirror 14 are limited by the level of miniaturization required. In a preferred embodiment, when mirror 14 is used, it can reflect back the light which is communicated from film 8 into the first end of second optical fiber 12.

Figure 2:
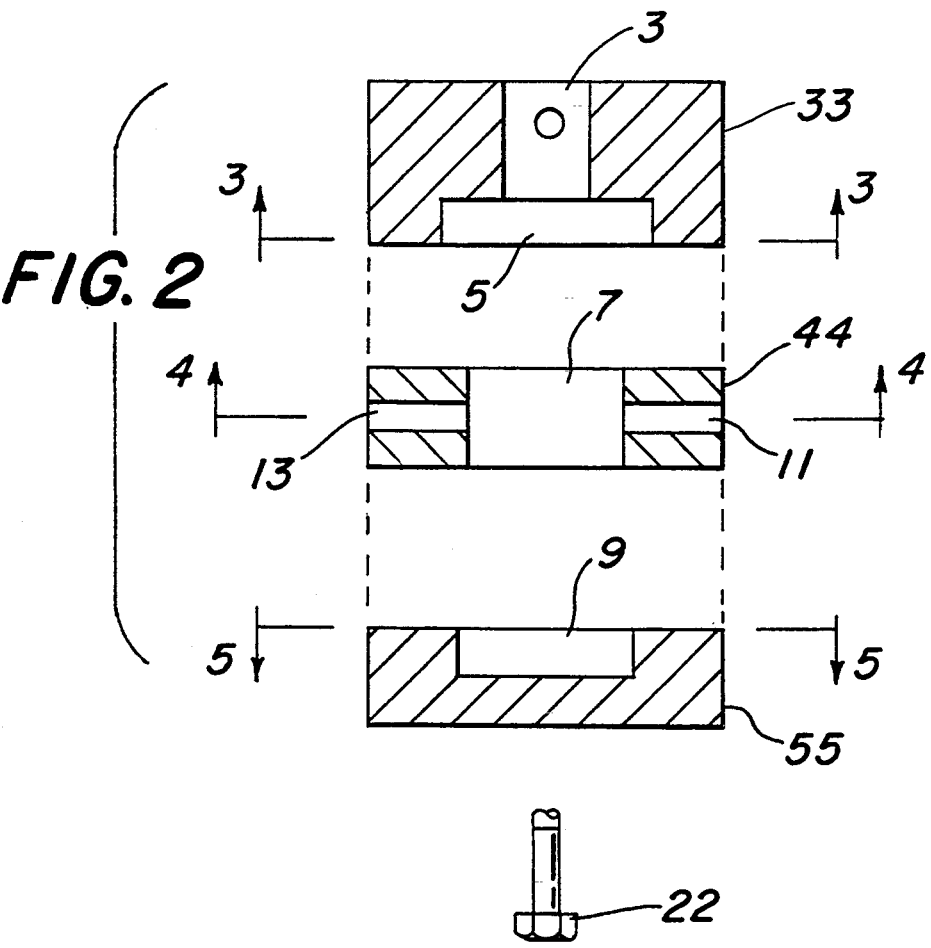
FIG. 2 is a cross-sectional view of the housing of a sensor of the present invention.
Figure 3:
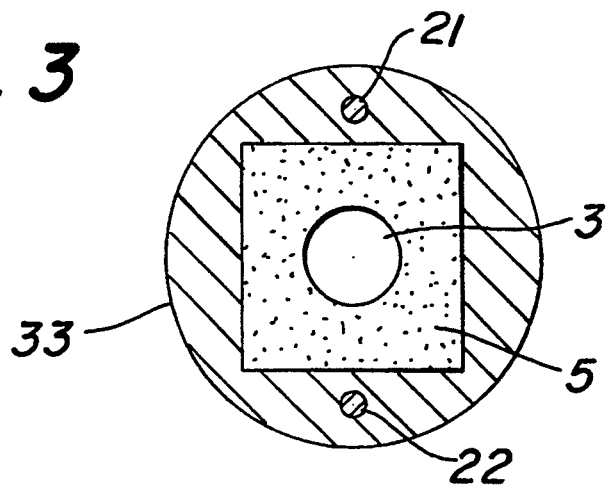
FIG. 3 is a cross-sectional view of the housing of a sensor of the present invention taken along the line 33—33 in FIG. 2.
Figure 4:
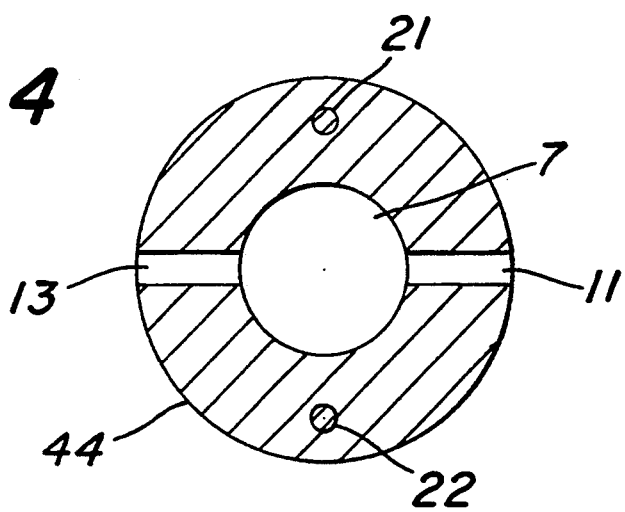
FIG. 4 is a cross-sectional view of the probe housing of a sensor of the present invention taken along the line 44—44 in FIG. 2.
Figure 5:
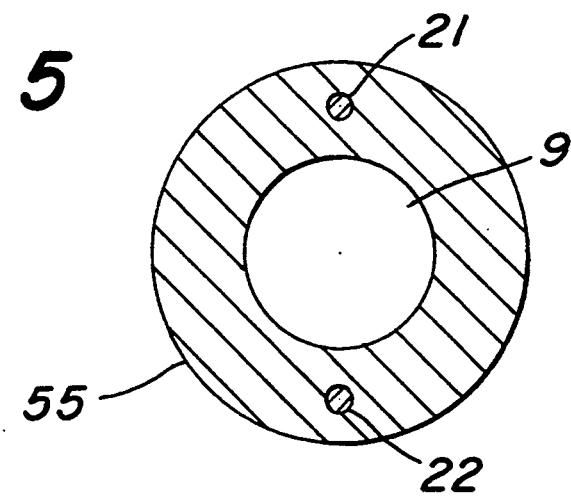
FIG. 5 is a cross-sectional view of the housing of a sensor of the present invention taken along the line 55—55 in FIG. 2.

FIG. 2 is a cross-sectional view of housing 4 of the sensor shown in FIG. 1. Housing 4 can be manufactured using for example polypropylene, nylon or teflon or of a metal such as for example aluminium or other reflective metal such as, for example, stainless steel. Generally, any metal can be used provided it is inert to the particular phase wherein moisture is being detected. Housing 4 can be cylindrical in shape and is comprised of a first, second and third sections 33, 44 and 55. FIGS. 3, 4, and 5 illustrate the cross-sectional views of first, second and third sections 33, 44 and 55 respectively. As shown in FIG. 2, first, second and third sections 33, 44, and 55 can be connected by means of first and second screws 21 and 22.

In an embodiment of the invention, first and second optical fibers 10 and 12 can be positioned into first opening 3 and can be stabilized by means of set screw 23. First opening 3 can be circular and can have a diameter at least as wide as the combined outer diameters of first and second optical fibers 10 and 12. First opening 3 connects with second opening 5. As shown in FIG. 1, second opening 5 can accommodate support 6 and can be sized accordingly.

Second section 44 is shown in FIGS. 2 and 4 and comprises third opening 7. As shown in FIG. 2, second section 44 also comprises first and second passages 11 and 13 which can allow the particular phase comprising the moisture to contact film 8. Third section 55 is shown in FIGS. 2 and 5, and comprises fourth opening 9 which can optionally accommodate mirror 14 as shown in FIG. 1. When mirror 14 is used, the distance 16 between the outer edge of second opening 5 and the outer edge of fourth opening 9 can be equivalent to the focal length of mirror 14.

Figure 6:
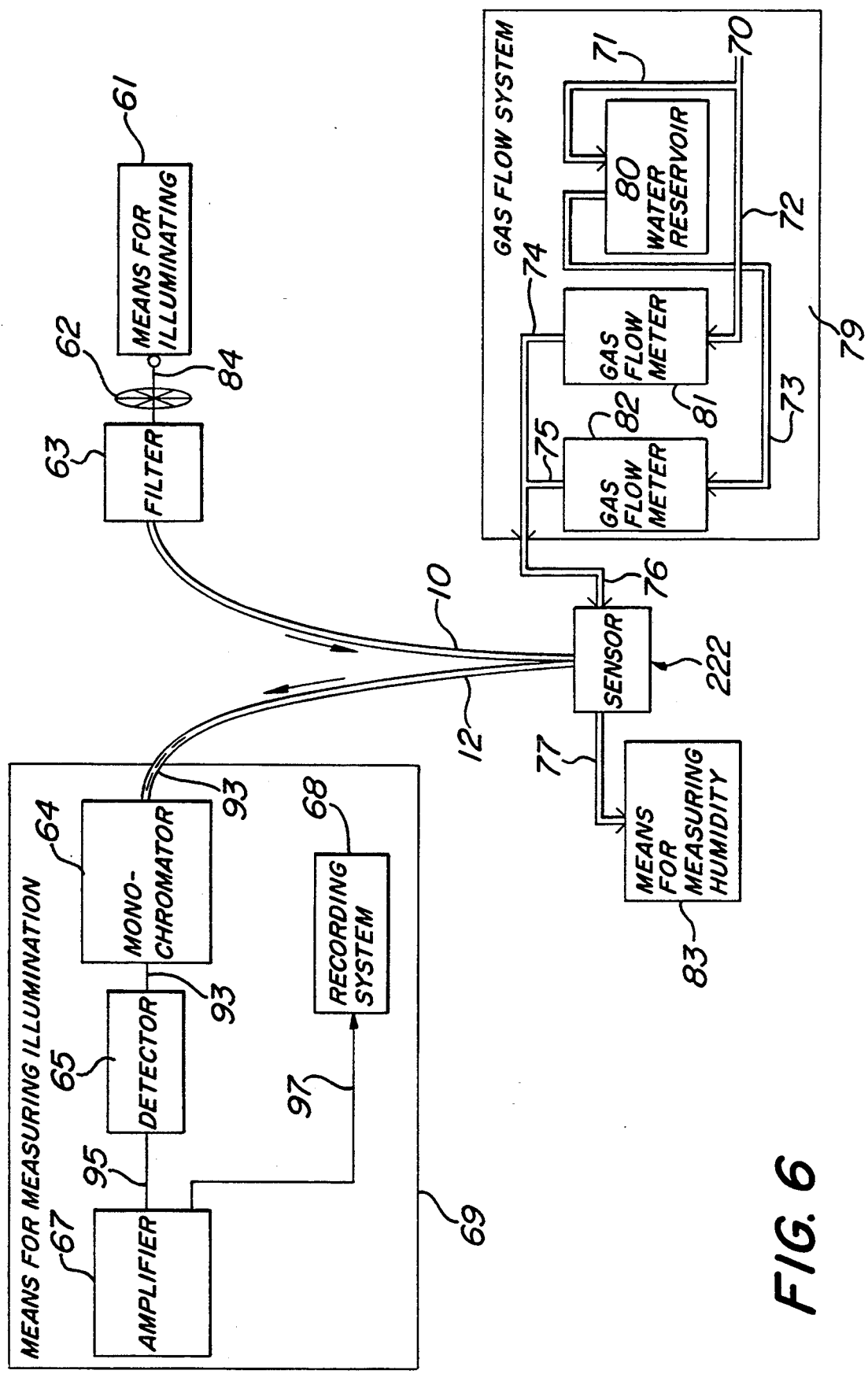
FIG. 6 is a diagram of an apparatus comprising a sensor of the present invention, means for illumination and means for measuring illumination.

Generally, with regard to instrumentation, FIG. 6 shows sensor 222 of the present invention, means for illuminating 61 the distal end of first optical fiber 10 and means 69 for measuring the illumination communicated at the distal end of second optical fiber 12. Sensor 222 comprises housing 4 and probe 2 as shown in FIG. 1. Means for illuminating 61 can be an illumination source such as a light source, (for example, a 100 W Xenophot HLX lamp by OSRAM, Germany). Means for illuminating 61 can emit light beam 84 which can be modulated by light chopper 62. Light chopper 62 can be a mechanical chopper (EG&G, model 196). After modulation, light beam 84 can be further modified by filter 63. Filter 63 can be, for example, a narrow bandpass filter characterized by a maximum transmission and bandwidth and can be appropriately selected such that its maximum transmission is compatible with the wavelength spectrum of the salt complex.

Means for measuring 69 can be comprised of a monochromator 64 (for example, Allied Analytical Systems, Model MonoSpec 27). Monochromator 64 can screen light beam 93 which can be emitted through second optical fiber 12 and can be used to select the desired wavelength range from light beam 93 for subsequent detection. Monochromator 64 can be calibrated with a light source with a known wavelength for example a He—Ne laser and can be set at a specific wavelength. Monochromator 64 can pass light beam 93 into detector 65. Detector 65 can be for example a photomultiplier tube and can be directly connected to monochromator 64. An output light beam 95 from detector 65 can be produced and can be detected by amplifier 67. Amplifier 67 can be a lock-in amplifier (EG&G amplifier Model 5209). Light beam 97 from amplifier 67 can be converted to a voltage signal and passed to recording system 68.

Recording system 68 can be for example a chart recorder or a personal computer. When recording system 68 is a computer (for example, IBM PC/AT), it can be equipped with a data acquisition software, a general purpose instrument bus and a Graphics card which can be directly connected to amplifier 67 through a plug-in cable. Recording system 68 can read the signal from amplifier 67 and can analyze it in the manner desired.

Figure 7:
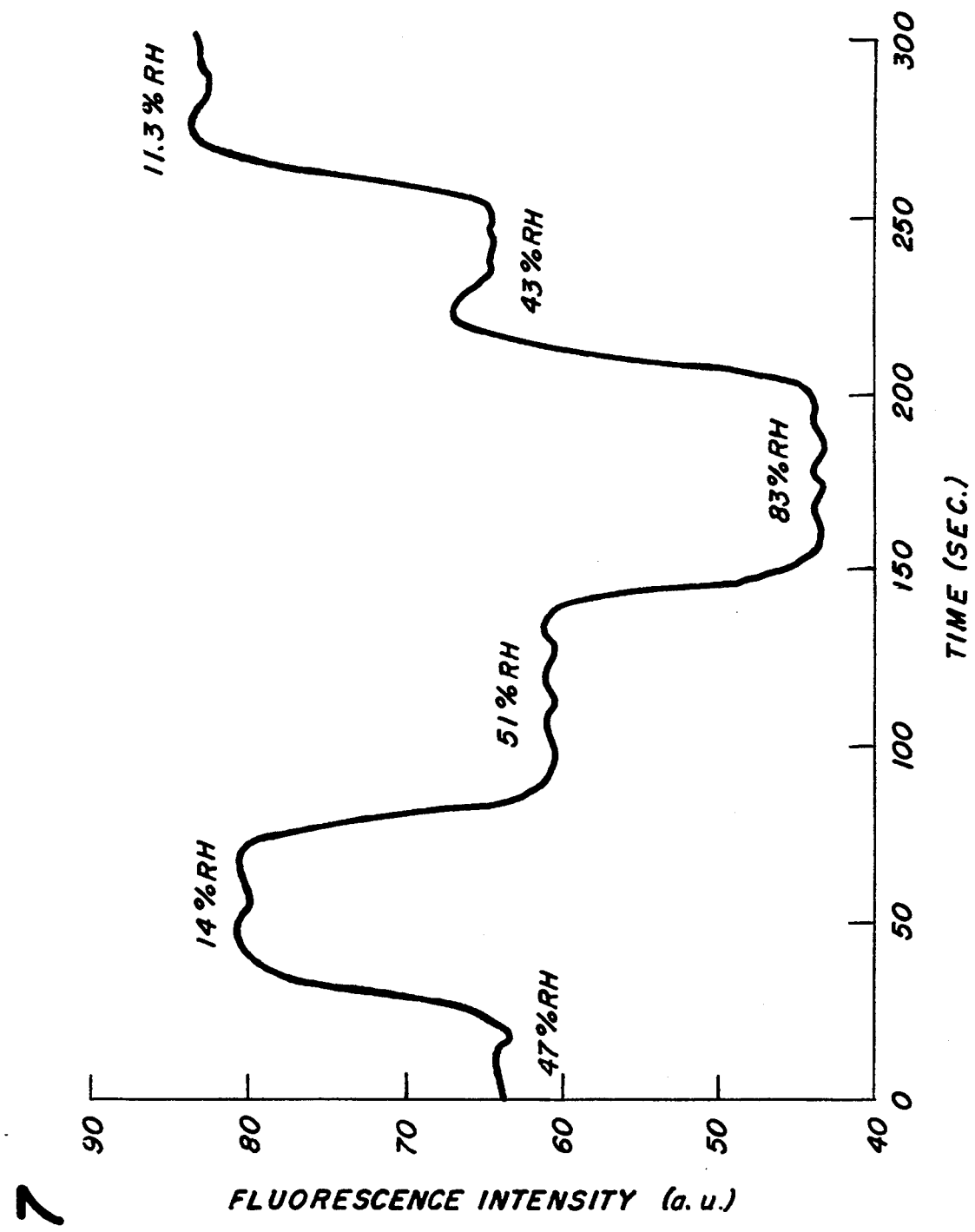
FIG. 7 is a plot of the response of a sensor of the present invention as measured by fluorescence in arbitrary units (a.u) as a function of time (sec) for different relative humidities (% RH).
Figure 8:
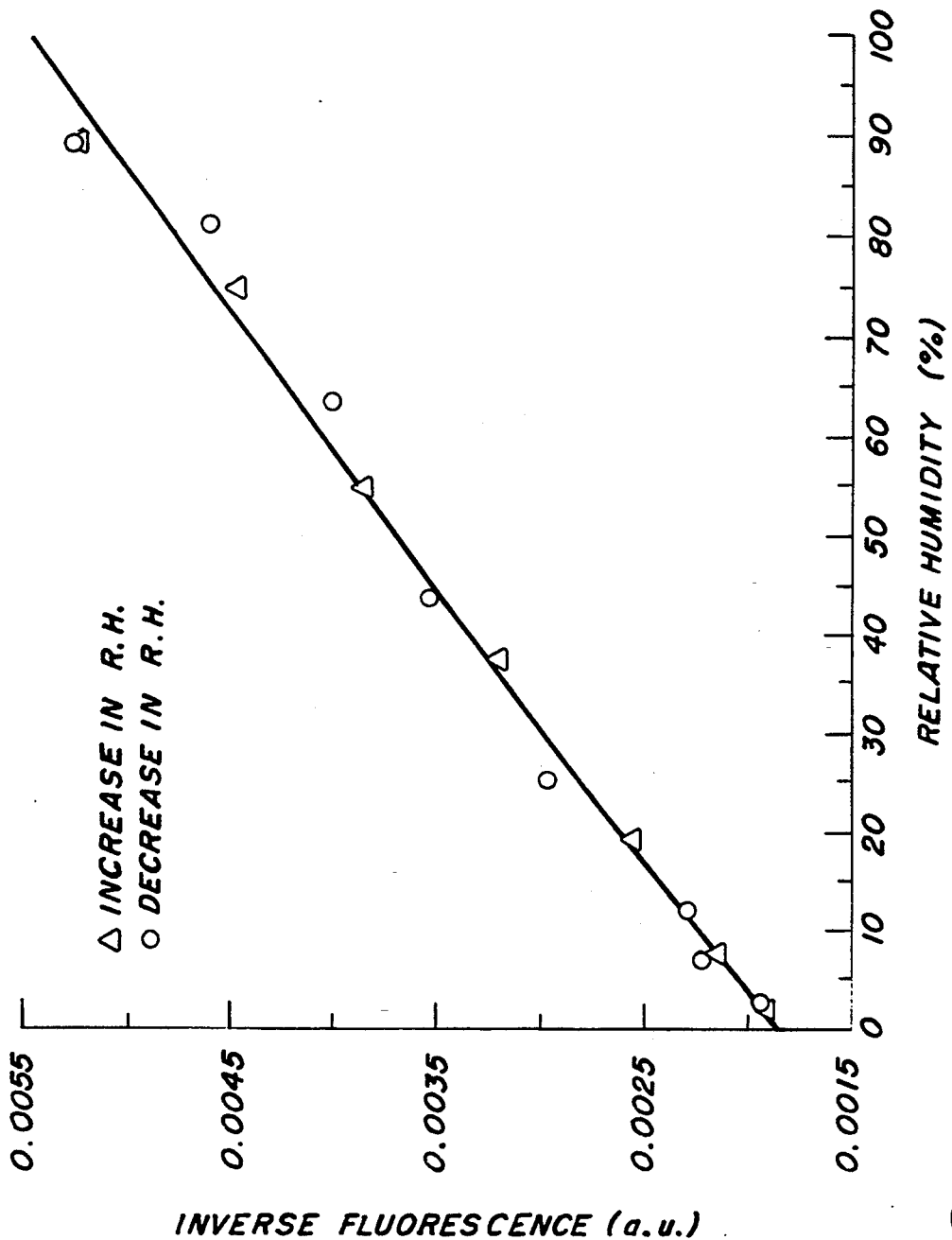
FIG. 8 is a plot of the response of a sensor of the present invention as measured by inverse fluorescence in arbitrary units (a.u.) as a function of increasing relative humidity ▲ and decreasing relative humidity ●.

In a preferred embodiment, as shown in FIG. 6, sensor 222 can be calibrated to detect different moisture levels. Several calibration techniques are known in the art and can be used to calibrate sensor 222. For example, sensor 222 can be connected to gas flow system 79. Gas flow system 79 can provide gas such as air or nitrogen which can comprise different moisture levels. Gas flow system 79 can be comprised of one or more flow meters 81 and 82. For example, in one particular embodiment, flow meters 81 and 82 can operate at a flow rate of about 500 ml/min, preferably about 100 ml/min. Other flow rates can be used depending on sensor 222 and the range of calibration required. In one operation of gas flow system 79, gas which can be either dry air or nitrogen can be introduced at inlet 70 and can enter water reservoir 80 through line 71 and can enter flow meter 81 through line 72. Gas which can be communicated through line 71 entrains water present in water reservoir 80 in the form of humidity and the gas which is now comprising a determined level of moisture leaves water reservoir 80 through line 73 and enters flow meter 82. The gas leaves flow meters 81 and 82 respectively through lines 74 and 75 and combines into line 76 to enter sensor 222 through opening 11. The gas leaves sensor 222 through opening 13 and enters means for measuring humidity 83, for example a hydrometer. When gas flows through sensor 222, changes in the moisture level can produce a corresponding change in the light signal as described above. Such change in the light signal can be recorded and the response of sensor 222 to different moisture levels as measured by relative humidity (% RH) can be obtained as shown in FIG. 7. In a preferred embodiment, when a salt complex of aluminium ion and morin is used in sensor 222, the light signal can be based on fluorescence. The fluorescence is quenched by moisture. Such quenching in turn produces changes in the signal which can be plotted using a linear relationship between inverse fluorescence and relative humidity. One example of a linear relationship is the Stern-Volmer equation as shown in FIG. 8. The linear relationship shown in FIG. 8 can be used as a calibration curve to measure moisture.

After calibration, sensor 222 can be used also as shown in FIG. 6 without gas flow system 79. A particular phase of interest which comprises moisture such as for example gas can be introduced into sensor 222 through passage 11 and can leave sensor 222 through passage 13. Similarly, when optional mirror 14 is not used, the particular phase of interest can contact film 8 directly.

As described above, when the moisture present in the phase of interest contacts the film, it quenches the fluorescence signal thereby producing a corresponding change in the light signal. Such changes in the light signal can be recorded and the response of sensor 222 to different moisture levels can be obtained as shown in FIG. 7. Results can be plotted as shown in FIG. 8 and the moisture level determined by comparison with a calibration curve.

This invention and many of its attendant advantages will be understood from the foregoing description, and it will be apparent that various modifications and changes can be made without departing from the spirit and scope of the invention or sacrificing all of its material advantages, the processes hereinbefore described being merely preferred embodiments. For example, the sensor can be useful for the measurement of humidity in many industrial processes such as prevalent in the food industry. The sensor can also be useful in the measurement of humidity in a steam environment. Other applications of the sensor include the measurement of water activity in liquid phases, in which case, a hydrophobic and water vapor permeable membrane can be used to separate the film from the aqueous solution such that the sensing material in the film is not dissolved in the aqueous solution. For applications of the sensor to the measurement of moisture in the gas phase, a membrane made for example from polytetrafluoride ethylene (PTFE) can be used thus allowing the passage of gas such as air, water vapor and other volatile compounds. In other applications, the sensor of the invention can be used to measure water activity in submerged or solid substrate fermentations.

What is claimed is:

1. A method for the measurement of the level of moisture in a gaseous phase utilizing an optical sensor, said sensor comprising a film of a polymer, said polymer having embedded therein a predetermined amount of a salt complex of a metal ion and an organic compound, wherein said salt complex emits fluorescence within a determined wavelength range, said polymer optically transparent in said wavelength range, and wherein said salt complex absorbs the moisture in said gaseous phase, the fluorescence emission being sensitive to quenching by said moisture, said method comprising the steps of:

contacting said optically transparent polymer with said gaseous phase;

introducing excitation light into the distal end of a first optical fiber and communicating said excitation light to said polymer through the proximal end of said first optical fiber to induce said fluorescence emission;

collecting said fluorescence emission into the proximal end of a second optical fiber;

detecting said fluorescence emission through the distal end of said second optical fiber;

measuring the quenching of said fluorescence emission; and determining the level of moisture in said gaseous phase.

* * * * *